United States Patent [19]

Matsumoto

[11] Patent Number: 4,848,896
[45] Date of Patent: Jul. 18, 1989

[54] EYE REFRACTOMETER

[75] Inventor: Kazuhiro Matsumoto, Kawasaki, Japan

[73] Assignee: Canon Kabushiki Kaisha, Tokyo, Japan

[21] Appl. No.: 929,413

[22] Filed: Nov. 12, 1986

[30] Foreign Application Priority Data

Nov. 25, 1985 [JP] Japan .................................. 60-264156

[51] Int. Cl.⁴ ............................................. A61B 3/10
[52] U.S. Cl. .................................................. 351/211
[58] Field of Search ......................................... 351/211

[56] References Cited

U.S. PATENT DOCUMENTS

| | | | |
|---|---|---|---|
| 2,114,984 | 4/1938 | Reason | 351/211 |
| 4,266,862 | 5/1981 | Trötscher et al. | 351/211 |
| 4,367,019 | 1/1983 | Kitao et al. | 351/211 |
| 4,390,255 | 6/1983 | Nohda et al. | 351/211 |
| 4,400,070 | 8/1983 | Isono et al. | 351/211 |
| 4,421,391 | 12/1983 | Matsumura et al. | 351/211 |
| 4,529,280 | 7/1985 | Nohda | 351/211 |
| 4,678,297 | 7/1987 | Ishikawa et al. | 351/211 |

Primary Examiner—John K. Corbin
Assistant Examiner—J. P. Ryan
Attorney, Agent, or Firm—Fitzpatrick, Cella, Harper & Scinto

[57] ABSTRACT

The present invention is directed to an eye refractometer, one embodiment of which, includes two-aperture stops positioned substantially conjugate with the pupil of the eye to be examined. Further, a two-dimensional light position detecting device is provided for detecting the two-dimensional positions of two light beams passed through the light beam incidence area of the pupil of the eye to be examined, reflected by the fundus of the eye to be examined and passed through the light exit area of the pupil of the eye to be examined. A processor is provided for obtaining the refractive value of the eye from the output of the two-dimensional light position detecting device.

9 Claims, 3 Drawing Sheets

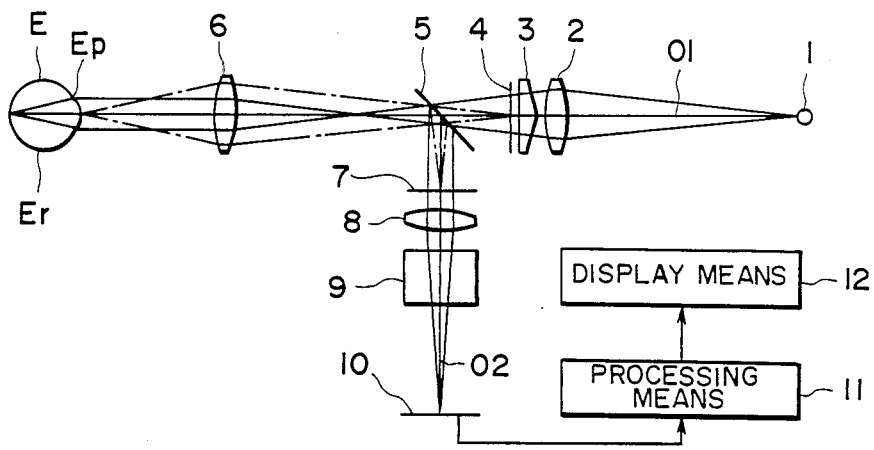
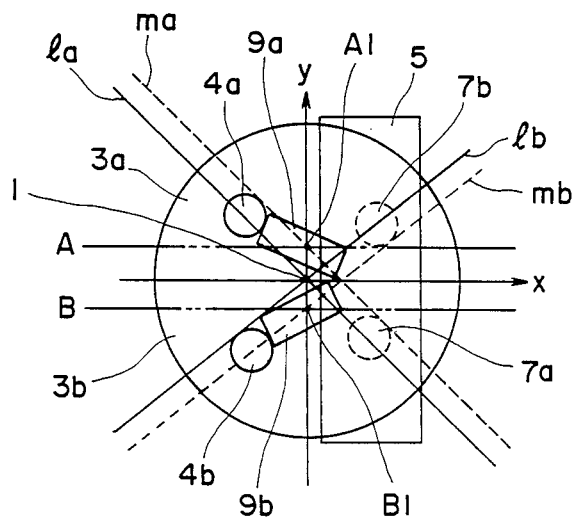
FIG. 1A
FIG. 1B

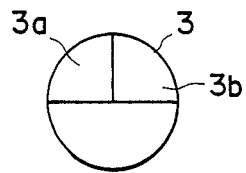
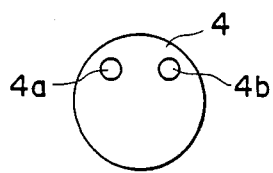
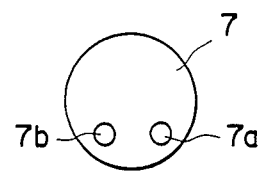
FIG. 2        FIG. 3        FIG. 4
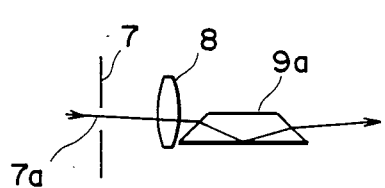
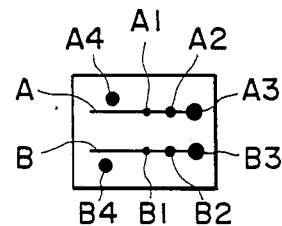
FIG. 5        FIG. 6A
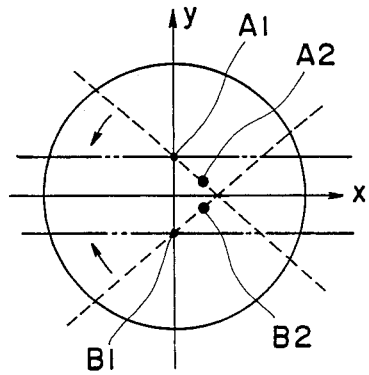
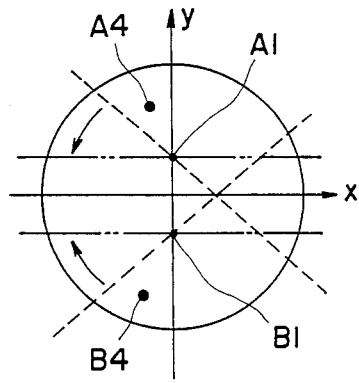
FIG. 6B        FIG. 6C
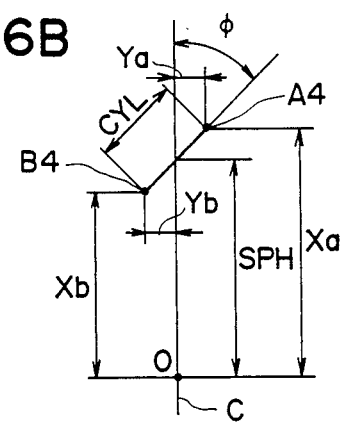
FIG. 7

EYE REFRACTOMETER

BACKGROUND OF THE INVENTION

1. Field of the Invention

This invention relates to an eye refractometer for measuring the degree of spherical refraction, the degree of astigmatic refraction, the astigmatic angle, etc. of an eye.

2. Related Background Art

The eye refractometer of this type, as is shown in the pending U.S. patent application Ser. No. 755,362, filed July 16, 1985, is such that the light from a light source is directed to an eye to be examined. The light is projected as a light source image onto the fundus of the eye. The light beams reflected from the fundus of the eye in at least three meridian directions on the pupil of the eye to be examined are taken out to thereby accomplish the measurement of the refraction of the eye in each meridian direction. However since it deals with the light beams in at least three meridian directions, it is considerably complicated in structure and relatively high in cost.

SUMMARY OF THE INVENTION

It is an object of the present invention to provide an eye refractometer which is structurally simple, compact and inexpensive.

BRIEF DESCRIPTION OF THE DRAWINGS

FIG. 1A shows the optical arrangement of a first embodiment of the present invention.

FIG. 1B is a view of the first embodiment as seen from the direction of the optic axis.

FIG. 2 is a front view of a deflecting prism.

FIGS. 3 and 4 are front views of two-aperture stops.

FIG. 5 illustrates an image rotating prism.

FIG. 6A illustrates the light beam on a light-receiving surface.

FIGS. 6B and 6C illustrate a case where astigmatism is absent and a case where antigmatism is present, respectively.

FIG. 7 illustrates the conversions from a light position into degree of spherical equivalence, degree of astigmatism and astigmatic angle.

FIGS. 8A and 8B to 11A and 11B show various modifications of a stop.

DESCRIPTION OF THE PREFERRED EMBODIMENTS

Figures 8A, 8B, 9A, 9B:
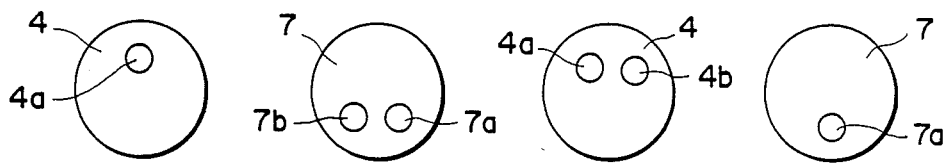

The invention will hereinafter be described in detail with respect to the shown embodiments thereof. The meridian directions include not only a direction passing through the optic axis as viewed from the direction of the optic axis, but also directions parallel thereto.

Referring to FIGS. 1A and 1B, on the optic axis 01 passing through a light source 1 and an eye E to be examined, there are disposed, in succession from the light source 1 side, a lens 2, a deflecting prism 3 for deflecting the image of the light source in the direction of the y-axis, a first two-aperture stop 4, a mirror 5 and an objective lens 6. The apertures 4a and 4b of the two-aperture stop 4 are disposed on the left side as shown in FIG. 1B, and the mirror 5 is provided only on the right side as shown in FIG. 1B. On the optic axis 02 on the reflection side by the mirror 5 of the light beam travelling from the eye E to be examined toward the light source, there are successively arranged a second two-aperture stop 7 provided with apertures 7a and 7b on the right side as shown in FIG. 1B, a lens 8, an image rotating prism 9 and a light-receiving element 10 which is a two-dimensional position detecting element. The light source 1 and the light-receiving surface of the light-receiving element 10 are substantially conjugate with the eye fundus Er of an emmetropia, and the first and second two-aperture stops 4 and 7 are substantially conjugate with the pupil Ep of the eye E to be examined.

The deflecting prism 3, as shown in FIG. 2, comprises two wedgeprisms 3a and 3b which correspond to the apertures 4a and 4b, respectively, of the first two-aperture stop 4 shown in FIG. 3. Use may be made of two light sources 1, instead of the deflecting prism 3 and the single light source 1. The apertures 4a and 4b of the first two-aperture stop 4 are substantially symmetrical with the apertures 7a and 7b of the second two-aperture stop 7 shown in FIG. 4 with respect to the center of the stop, i.e., the center of the pupil Ep. The mirror 5, as previously mentioned, is disposed on one side with respect to the optic axis 01 and separates the light beams passing through the first two-aperture stop 4 and the second two-aperture stop 7. The image rotating prism 9 comprises two prisms 9a and 9b and, as is partly shown in FIG. 5, correspondingly to the apertures 7a and 7b of the second two-aperture stop 7, the two prisms are rotatively displaced by a predetermined angle and disposed so that the direction la, ma is the direction A and the direction lb, mb is the direction B.

Thus, the light beam emitted from the light source 1 passes through the lens 2, the deflecting prism 3, the first two-aperture stop 4 and the objective lens 6 to the eye E to be examined, and the reflected light reflected by the eye fundus Er passes through the objective 6 and is reflected toward the optic axis 02 by the mirror 5 and passes through the second two-aperture stop 7, the lens 8 and the image rotating prism 9 to the light-receiving surface of the light-receiving element 10.

In FIG. 1B, where the eye E to be examined is an emmetropia, the image of the light source 1 on the eye fundus is caused by the deflecting prisms 3a and 3b to assume positions A1 and B1 displaced in the direction of the y-axis from the optic axis 01. Where the eye E to be examined is an eye of abnormal refraction free of astigmatism, the image of the light source 1 passes through the positions A1 and B1 and is displaced on the directions ma and mb parallel to the measurement meridian directions la and lb, respectively. Where the eye E to be examined has astigmatism, the image of the light source 1 is displaced in a direction perpendicular to the measurement meridian directions.

FIG. 6A shows the state of the light beam on the light-receiving element 10. Where the eye E to be examined has no astigmatism, the two light beams rotated by the image rotating prism 9 travel on parallel straight lines A and B while blurring as indicated by A1, A2, A3 and B1, B2, B3 in conformity with the refractive power of the eye E to be examined as illustrated in FIG. 6B, and the refractive power of the eye E can be found from the amount of travel. Where the eye E to be examined has astigmatism, the light beams travel in the direction of travel in the case where astigmatism is absent and in a direction perpendicular thereto. By taking the amount of travel in this perpendicular direction also into consideration, that is, from the information of the amounts of travel in the two meridian direction and the information of the amounts of travel in the directions perpendicular to the two meridian directions, the degree of astigmatism and the astigmatic angle of the eye E to be examined can be found even if measurement is not effected with respect to three meridians. As shown in FIG. 1, operation is carried out by processing means 11 and the result of the operation is displayed by display means 12.

Reference is now had to FIG. 7 to describe the method of calculation. Straight lines A and B are caused to overlap each other to form a straight line C. For simplicity, the two meridian directions in which the light beam is taken out are made perpendicular to each other on the pupil of the eye to be examined, as shown in FIGS. 1A and 1B. Point 0 is the position of the light beam at 0 diopter. When the distances of movement of points A4 and B4 from 0 diopter in the direction of the straight line C are Xa and Xb, and the distances of movement of these points in a direction perpendicular thereto are Ya and Yb, and the angle formed between a straight line passing through the points A4 and B4 and the straight line C is $\phi$, and the angle constant, i.e., the angle formed between the horizontal direction which is the reference direction in the ophthalmic examination and the measurement meridian direction is $\beta$, then the degree of spherical equivalence SPH, the degree of astigmatism CYL and the astigmatic angle Ax are given as follows:

$$SPH = D \cdot (Xa+Xb)/2$$

$$CYL = D\sqrt{\{(Xa-Xb)^2+(Ya+Yb)^2\}^{\frac{1}{2}}}$$

$$AX = (\phi/2)+\beta = (\tfrac{1}{2})\cdot\tan^{-1}\{(Ya+Yb)/(Xa-Xb)\}+\beta$$

where D is a coefficient corresponding to the diopter of unit distance. Even if the two meridian directions are not made perpendicular to each other, it is easy to calculate these three amounts. Also, it is unnecessary to know the aforementioned four amounts of movement Xa, Xb, Ya and Yb, and it is sufficient to measure three of them.

Figures 10A, 10B, 11A, 11B:
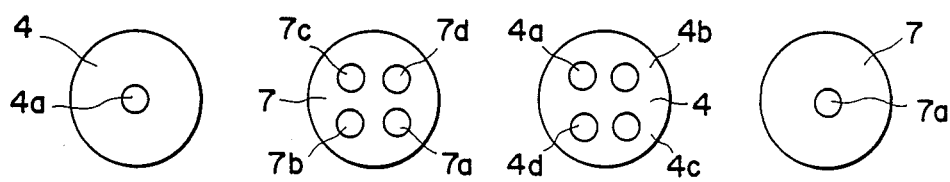
Figure 12:
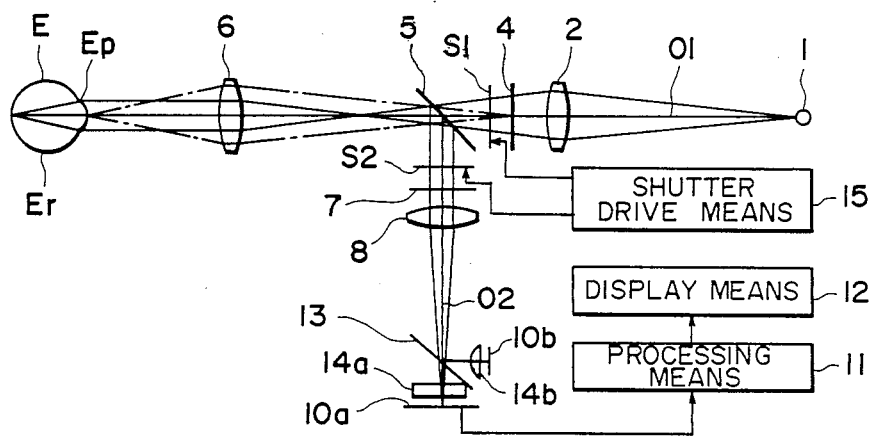
FIG. 12 shows the optical arrangement of a second embodiment of the present invention.

Now, in the above-described embodiment, the two-aperture stops 4 and 7 have been used to project or take out two light beams, but as shown in FIGS. 8A and 8B and FIGS. 9A and 9B, the number of apertures in one of the stops 4 and 7 may be one. The position of this aperture may be on or off the optic axis.

Where the number of apertures in the stop 4 is one, the deflecting prism 3 becomes unnecessary, and this leads to an optically simple structure. Also, of the light beams in two meridian directions, the light beams passing through the apertures of the stop 4 or the stop 7 are alternately shut off, whereby they are projected or taken out while being distinguished from each other in time, whereby the deflecting prism 3 can be made unnecessary. As shown in FIGS. 10A and 10B, a light beam may be projected from the vicinity of the center of the pupil to the central portion of the eye fundus Er, whereby four light beams may be taken out as the light beams in two meridian directions from two sets of optic-axis symmetrical points around the pupil, i.e., off the optic axis. That is, in this case, the reflecting position of the light beam on the eye fundus Er is always near the center of the eye fundus Er and two pieces of information in two meridian directions are obtained, and in each meridian direction, measurement can be accomplished depending not on the absolute position of a light beam but on the spacing between two light beams, i.e., the relative position of the two light beams, and thus, a highly reliable measured value can be obtained. The incidence and emergence may be reversed to each other as shown in FIGS. 11A and 11B. Further, the light-receiving element 10 need not always be a simple two-dimensional light position detecting element, but may be one-dimensional light position detecting elements 10a and 10b combined together perpendicularly to each other in the measurement meridian directions (the directions 1a and 1b of FIG. 1B) with a beam splitter 13 interposed therebetween, as shown in FIG. 12. For example, two one-dimensional light position detecting elements 10a and 10b may be combined into the shape of a cross, and two cylindrical lenses 14a and 14b whose bus line directions coincide with the measurement meridian directions may be provided in the optical path on this side of the one-dimensional light position detecting elements to thereby enlarge the light-receiving width, and shutters S1 and S2 may be driven by shutter drive means 15 so that light beams may alternately pass through the openings in the respective measurement meridian directions and be projected onto the one-dimensional light position detecting elements, whereby the two-dimensional position may be found.

I claim:

1. An eye-refractometer comprising:
    index light beam projecting means for projecting an index light beam onto the eye-fundus of an eye to be examined for measuring a refractive power of the eye to be examined;
    a two-dimensional light position detecting means for detecting the position of the index light beam which is scatteringly reflected by the eye fundus, said detecting means being positioned substantially conjugate with the eye-fundus;
    a stop means mounted to be positioned substantially conjugate with the pupil of the eye to be examined, said stop means having at least a first aperture for receiving incident light beams directed to the eye, at least a second aperture for receiving reflected light beams from the eye and at least a third aperture for receiving one of incident light beams directed to the eye and reflected light beams from the eye, said first, second and third apertures being spaced from each other such that at least two lines are formed extending between first, second and third apertures;
    said two-dimensional detecting means including means for generating at least three data among positional data of the reflected index light beam parallel with the first line, data orthogonal to the first line, data parallel with the second line and data orthogonal to the second line; and
    a calculating means for calculating an eye-refraction power on the basis of said at least three data.

2. An eye refractometer according to claim 1, wherein said third aperture receives incident light beams.

3. An eye refractometer according to claim 1, further including at least four apertures, each aperture receiving one of incident light beams and reflected light beams.

4. An eye refractometer according to claim 1, wherein a fixed image rotating prism corresponding to the light beam exit area is provided in the light beam exit optical path from the eye to be examined.

5. An eye refractometer according to claim 1, wherein said two-dimensional light position detecting means comprises two one-dimensional light position detecting means provided so as to assume a cross-shape to each other at positions with a beam splitter interposed therebetween.

6. An eye refractometer comprising:
a light beam separating means mounted to be positioned substantially optically conjugate with a pupil of an eye to be examined, said light beam separating means including means for forming at least a first light incidence area, a first light exit area and at least one of a second light incidence area and a second light exit area for forming a first line and a second line extending between the light beam incidence areas and the light beam exit areas;
a two-dimensional light position detecting means for detecting the two-dimensional positions of two light beams passed through the light beam incidence area of the pupil of the eye to be examined, reflected by the fundus of the eye to be examined and passed through the light beam exit area of the pupil of the eye to be examined; and
a processing means for obtaining the refractive value of the eye from the output of said two-dimensional light position detecting means,
wherein a deflection prism having a deflecting surface corresponding to the light beam incidence area is provided in the light beam incidence optical path to the eye to be examined.

7. An eye refractometer according to claim 6, wherein a fixed image rotating prism corresponding to the light beam exit area is provided in the light beam optical path reflected from the eye to be examined.

8. An eye refractometer, comprising:
a light beam separating means mounting to be positioned substantially optically conjugate with the pupil of the eye to be examined, said light beam separating means including means for forming at least a first light incidence area, a first light beam exit area, and at least one of a second light beam incidence area and a second light beam exit area for forming a first line and a second line when connecting the light beam incidence areas and the light beam exit areas;
a two-dimensional light position detecting means for detecting the two-dimensional positions of the two light beams passed through the light beam incidence areas, reflected by the fundus of the eye to be examined and passed through the light beam exit areas; and
a processing means for obtaining the refractive value of the eye from the output of said two-dimensional light position detecting means;
wherein means is provided for time-dividing the light beam incident on said two-dimensional light position detecting means.

9. An eye refractometer comprising:
a light beam separating means mounted to be positioned substantially optically conjugate with the pupil of an eye to be examined, said light beam separating means including means for forming at least a first light beam incidence area, a first light beam exit area and at least one of a second light beam incidence area and a second light beam exit area such that first and second lines are formed extending between the light beam incidence areas and the light beam exit areas;
a two-dimensional light position detecting means including two one-dimensional light position detecting means provided so as to together assume a cross-shape at positions with a beam splitter interposed therebetween for detecting the two-dimensional positions of two light beams passed through the light beam incidence area, reflected by the fundus of the eye to be examined and passed through the light beam exit area; and
a processing means for obtaining the refractive value of the eye from the output of said two-dimensional light position detecting means,
wherein a cylindrical lens whose bus line direction coincides with the measurement direction is provided on one side of each of said one-dimensional light position detecting means.

* * * * *

UNITED STATES PATENT AND TRADEMARK OFFICE
CERTIFICATE OF CORRECTION

PATENT NO. : 4,848,896

DATED : July 18, 1989

INVENTOR(S) : Kazuhiro Matsumoto

It is certified that error appears in the above-identified patent and that said Letters Patent is hereby corrected as shown below:

COLUMN 1
    Line 41, change "antigmatism" to --astigmatism--.

COLUMN 2
    Line 37, change "objective 6" to --objective lens 6--.

COLUMN 3
    Line 2, change "direction" to --directions---.
    Line 32, change "CYL = $D \sqrt{\{(X_a-X_b)^2 + (Y_a+Y_b)^2\}^{1/2}}$" to --CYL = $D \cdot \{(X_a-X_b)^2 + (Y_a+Y_b)^2\}^{1/2}$--.

COLUMN 4
    Line 27, change "eye-refractometer" to --eye refractometer--.

COLUMN 5
    Line 36, change "mounting" to --mounted--.
    Line 40, change "first light incidence area" to --first light beam incidence area--.

Signed and Sealed this

Eighteenth Day of September, 1990

*Attest:*

HARRY F. MANBECK, JR.

*Attesting Officer*      *Commissioner of Patents and Trademarks*